United States Patent
Pfeiffer et al.

(10) Patent No.: US 6,264,613 B1
(45) Date of Patent: Jul. 24, 2001

(54) SITE CODING FOR MEDICAL DEVICES FOR INTRODUCTION INTO A PATIENT'S BODY

(75) Inventors: Urich J. Pfeiffer, Munich; Ernst-Peter Salfeld, Albisheim, both of (DE)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/401,894

(22) Filed: Sep. 23, 1999

(30) Foreign Application Priority Data

Sep. 25, 1998 (EP) ................................. 98118188
Apr. 26, 1999 (EP) ................................. 99108146

(51) Int. Cl.[7] ................................. A61B 5/02; A61B 5/04
(52) U.S. Cl. .................. 600/505; 600/486; 600/394; 600/381
(58) Field of Search ................. 600/505, 504, 600/507, 481, 485, 486, 488, 508, 459, 462, 466, 467, 468, 465, 479, 480, 394, 393, 372, 373, 374, 381, 300

(56) References Cited

U.S. PATENT DOCUMENTS

| | | | |
|---|---|---|---|
| 4,407,298 | * 10/1983 | Lentz et al. ................... | 600/526 |
| 4,611,601 | * 9/1986 | Bowman ...................... | 600/486 |
| 4,858,615 | * 8/1989 | Meinema ...................... | 600/481 |
| 5,058,588 | * 10/1991 | Kaestle ...................... | 600/310 |
| 5,205,281 | * 4/1993 | Buchanan ..................... | 600/310 |
| 5,720,293 | 2/1998 | Quinn et al. . | |
| 6,113,547 | * 9/2000 | Catallo et al. ................ | 600/459 |
| 6,142,946 | * 11/2000 | Hwang et al. ................. | 600/459 |

FOREIGN PATENT DOCUMENTS

| | | |
|---|---|---|
| 0079086A1 | 10/1982 | (EP) . |
| 0329196A2 | 8/1983 | (EP) . |
| WO93/15652 | 7/1992 | (WO) . |

\* cited by examiner

*Primary Examiner*—Eric F. Winakur
*Assistant Examiner*—Navin Natnithithadha

(57) ABSTRACT

Disclosed is a medical device for introduction into a patient's body, in particular into the patient's blood vessel, for measuring a physiological parameter. The medical device comprises means for coding the site of an application of the medical device in the patient's body and/or means for coding the effect of the site of an application of the medical device in the patient's body on the measurement of the physiological parameter.

22 Claims, 5 Drawing Sheets

US 6,264,613 B1

SITE CODING FOR MEDICAL DEVICES FOR INTRODUCTION INTO A PATIENT'S BODY

FIELD OF THE INVENTION

The present invention relates to medical devices, such as catheters, sensors, transducers, or the like, for introduction into a patient's body, in particular the patient's blood vessel, for measuring one or more physiological parameter(s), and to connectors for connecting the medical devices.

BACKGROUND OF THE INVENTION

Catheters represent the most common medical devices for introduction into a patient's body. A catheter, in general, is a tubular medical device for insertion into canals, vessels, passageways, or body cavities usually to permit injection or withdrawal of fluids or to keep a passage open or to carry sensors. Catheters are often applied for determining blood flow and/or volumetric hemodynamic parameters with thermodilution techniques, or for invasive blood pressure and/or oxygen saturation measurements with embedded fiber optics.

Thermodilution catheters, as typical examples for catheters, are well known in the literature and medical practice for determining blood flow, cardiac blood volumes, or pulmonary blood volumes. Such catheters are typically small diameter catheters for insertion in blood vessels, carrying distal temperature sensing means with more or less additional lumens, to inject the dilution liquid and/or to transmit a blood pressure in a vessel at a distal opening to a proximal opening for pressure sensing means. A common characteristic of the thermodilution measurements is the injection of a cold bolus and to sense the temperature displacement downstream with the temperature sensing means of the catheter. From the magnitude, duration, appearance time, mean transit time, and down slope time of the temperature displacement curve, flow and volume parameters of organs or parts thereof between site of bolus injection and site of temperature sensing are derived by appropriate measurement algorithms of a general purpose processing device. A representative thermodilution catheter is illustrated in U.S. Pat. No. 3,995,623.

FIG. 1 illustrates a conventional thermodilution catheter 2 for insertion by central venous access through the right heart into the pulmonary artery. The catheter 2 comprises a distal tip orifice 1, communicates through an internal lumen of the catheter 2, and terminates in a luer fitting 3. A balloon 4 communicates through an internal lumen of the catheter 2 and terminates in a syringe 5 for the purpose of inflating the balloon. A thermistor 6 is connected by small wires embedded in a wall of catheter 2 to dedicated pins in a catheter connector 7. An injectate orifice 8 communicates through an internal lumen of the catheter 2 and terminates in a luer fitting 9.

FIG. 2 illustrates a conventional thermal dilution catheter 2 for insertion by an arterial access into an aortic or near an aortic vessel. The catheter 2 comprises the same characteristics as in FIG. 1, however, without the balloon 4, the syringe 5 including internal lumen, the injectate orifice 8, and luer fitting 9 including internal lumen.

FIGS. 3A and 3B illustrate in detail an example of the electrical catheter connector 7 as used e.g. by the Hewlett-Packard HP M1642A Catheter Interface Cable. The lug of the catheter connector 7 in FIG. 3A comprises electrical contact pins 10 enclosed by a threaded collar 11. A corresponding device connector socket 7A in FIG. 3B is adapted to receive the catheter connector plug of FIG. 3A. In FIG. 3B, a device connector 14 includes electrical pin receptors 10A and a threaded slip collar 15 to secure the connection of the connectors 7 and 14.

Thermodilution catheters today are used most widely to determine blood flow and pressures in the pulmonary artery. Such catheters are inserted via a central venous access like the right internal jugular vein or left subclavian vein through the right heart and placed with the distal end in the pulmonary artery. The rate of blood flow is computed from the displacement of blood temperature according to the Stewart-Hamilton dilution equation for a thermal indicator as described in U.S. Pat. No. 3,987,788 or in the publication "The thermodilution method for the clinical assessment of cardiac output", J. R. C. Jansen, Intensive Care Med (1995) 21:691–697. In another application, the transpulmonary thermodilution technique, the thermodilution catheter is located in the arterial side of the vascular system and placed via a femoral, radial or axillary artery access. In addition to the derived blood flow calculation the circulatory filling status can be determined from the appearance time, mean transit time and down slope time of the blood temperature displacement as described in the U.S. Pat. No. 5,526,817.

It has been shown that erroneous applications of catheters, e.g. due to a wrong placement in the intra-vascular system or selection of the measurement parameters, can lead to wrong measurement results and might cause serious harm to the patients, e.g. due to a wrong therapeutic decision based on the wrong results.

SUMMARY OF THE INVENTION

It is therefore an object of the invention to reduce the risk of erroneous catheter measurements. The object is solved by the independent claims. Preferred embodiments are shown by the dependent claims.

It has been found that physiological parameters measured within the patient's body exhibit different characteristics dependent on the respective measuring site, i.e. the spatial location of the measuring device. In particular for applications of thermal dilution catheters (cf. e.g. FIG. 1), the spatial location of the place of injection of the cold bolus and the place of sensing of the temperature displacement represents a strong influence on the measurement. Coding the application site thus allows a measurement evaluation algorithm to take into consideration the different application sites. In particular, the size-coding allows to automatically set characteristic measurement parameters dependent on the site-coding, so that a correct parameter setting and algorithm selection can be ensured or, in other words, that the risk of erroneous catheter applications can be reduced.

The site coding can be accomplished by any means as known in the art such as electronically, mechanically, optically or combinations thereof.

The site coding, in general, provides the possibility to optimize and/or adapt the measuring behavior on the respective measuring site. Signal modifications due to influences of the respective site of measurement can be automatically corrected. Specific measuring or measurement evaluation modules for providing specific results can be automatically enabled or disabled dependent on the site coding.

The site coding according to the invention allows a precise definition of the measurements the medical device is dedicated for or, in other words, to clearly define which parameters will be processed and displayed with a connected processing unit.

The invention also allows automatically adapting a measurement on the specific conditions and influences of a respective measurement site, e.g. in a way that the measurement results are automatically evaluated in accordance with the setting of the site coding. This renders the possibility, for example, to adapt the measurement results to specific measurements characteristics determined by the respective measurement site e.g. for adapting the sensing resolution to the signal strength at the coded site. Accordingly, marking or "labeling" the measurement with a specific label, e.g. "CVP" for a pressure at central venous access or "ABP" for a blood pressure at arterial access, can thus be achieved.

Additionally, site coding according to the invention allows providing information about possible parameters to be measured in a specific site.

Furthermore, the inventive site coding renders the possibility to automatically provide information about the specific embodiment of the medical device, e.g. information how the medical device is embodied with respect to the specific measuring site.

In addition to the coding of the respective measurement site, further information such as country specific embodiments can be automatically provided to the measurement evaluation device, allowing to automatically adapt e.g. differing accuracy specifications, parameter units (e.g. Celsius or Fahrenheit), and so on.

Also, user warnings by a wrongly placed catheter dedicated to another specific site are possible by such site coding due to measurement variables outside of definable limits.

BRIEF DESCRIPTION OF THE DRAWINGS

Other objects and many of the attendant advantages of the present invention will be readily appreciated and become better understood by reference to the following detailed description when considering in connection with the accompanied drawings. Features that are substantially or functionally equal or similar will be referred to with the same reference sign(s).

DETAILED DESCRIPTION OF THE INVENTION

Figure 1:
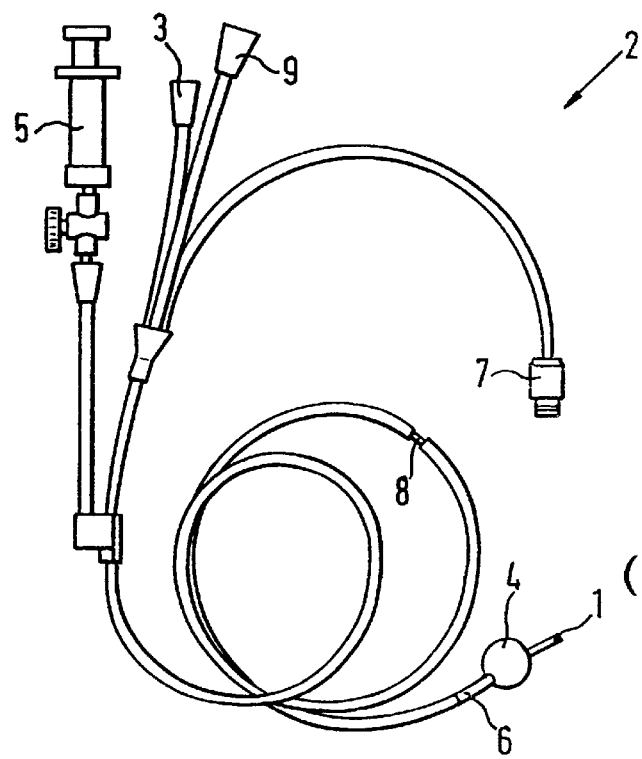
FIG. 1 shows a perspective view of a representative conventional pulmonary artery thermodilution catheter.
Figure 2:
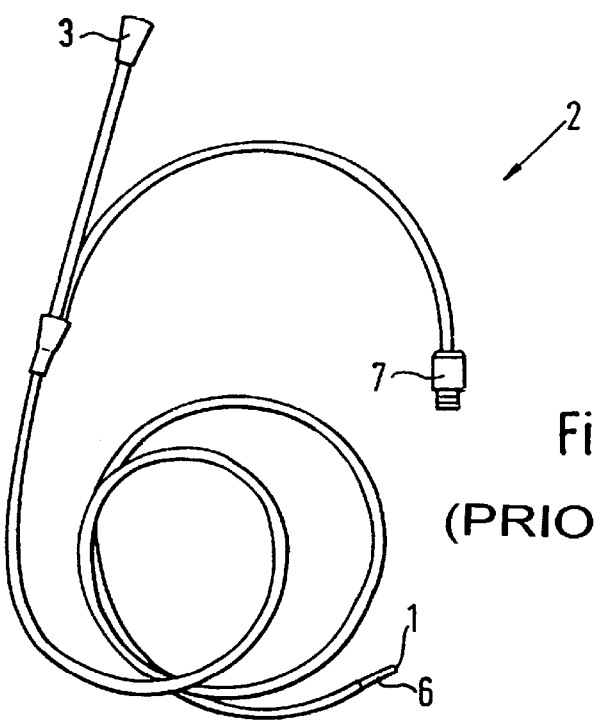
FIG. 2 shows a perspective view of a representative conventional arterial thermodilution catheter.
Figure 3A:
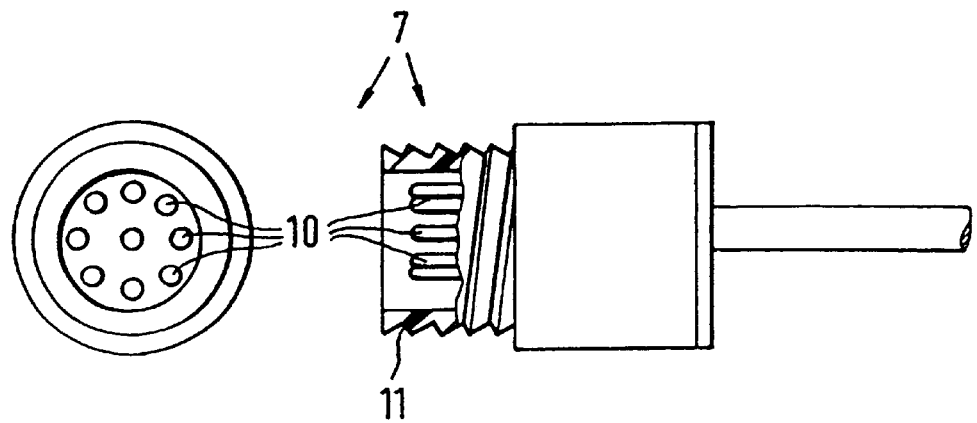
FIG. 3 provides side and end views of the catheter plug and receiving connector socket of the catheters in FIGS. 1 or 2.
Figure 3B:
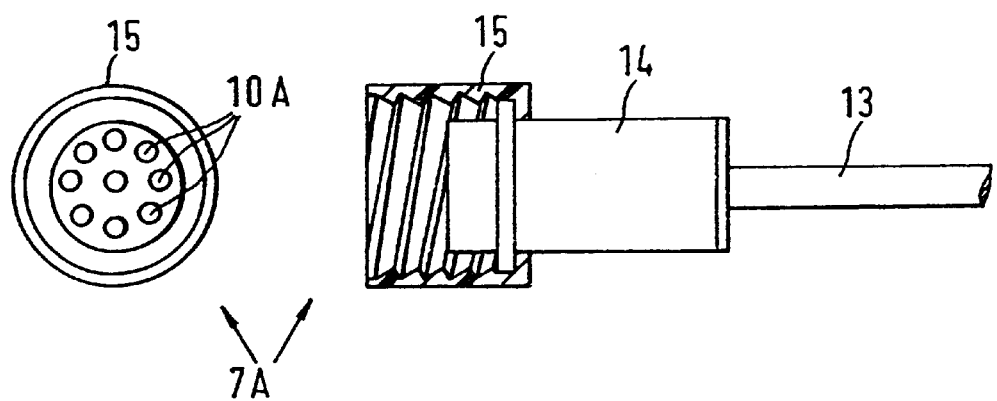

The invention shall now be explained for the example of the thermodilution catheter 2 as depicted e.g. in FIGS. 1–3. However, it is to be understood that the principle of the invention is applicable to any kind and type of medical device for introduction into a patient's blood vessel for measuring a physiological parameter.

The spatial location or site of a thermodilution catheter placement into the cardiovascular system defines the measurable parameters within their characteristics requiring different appropriate algorithms in a processing device. For such applications of thermodilution catheters, the physical size of a catheter assembly may differ in length, diameter, lumens, and features.

The present invention provides dedicated thermodilution catheters with electrical connectors coded to communicate the designated site of catheter placement to the processing device, thereby allowing the processing device to select the appropriate algorithms for parameter computation. The catheter connector preferably is multi-pinned plug assembly including pins for indicating site of placement in accordance with corresponding encoding means coupled between those pins.

The thermodilution catheter of the present invention may also include blood pressure measurement or bolus injection capability via one or more lumens opening through the wall of the catheter.

If a non-standard site for thermodilution catheter placement is used, a combination of appropriate algorithm can be selected manually.

According to the invention, a thermodilution catheter assembly for use in hemodynamic monitoring contains encoding means for encoding the type of measurement the catheter is dedicated. In a preferred embodiment, the encoding means housed in the connector of the catheter assembly automatically communicates the type of measurement to a processing device when the connection is made. The processing device uses this information to select the appropriate measurement algorithms for the connected catheter to compute possible measurement parameters.

Figure 4:
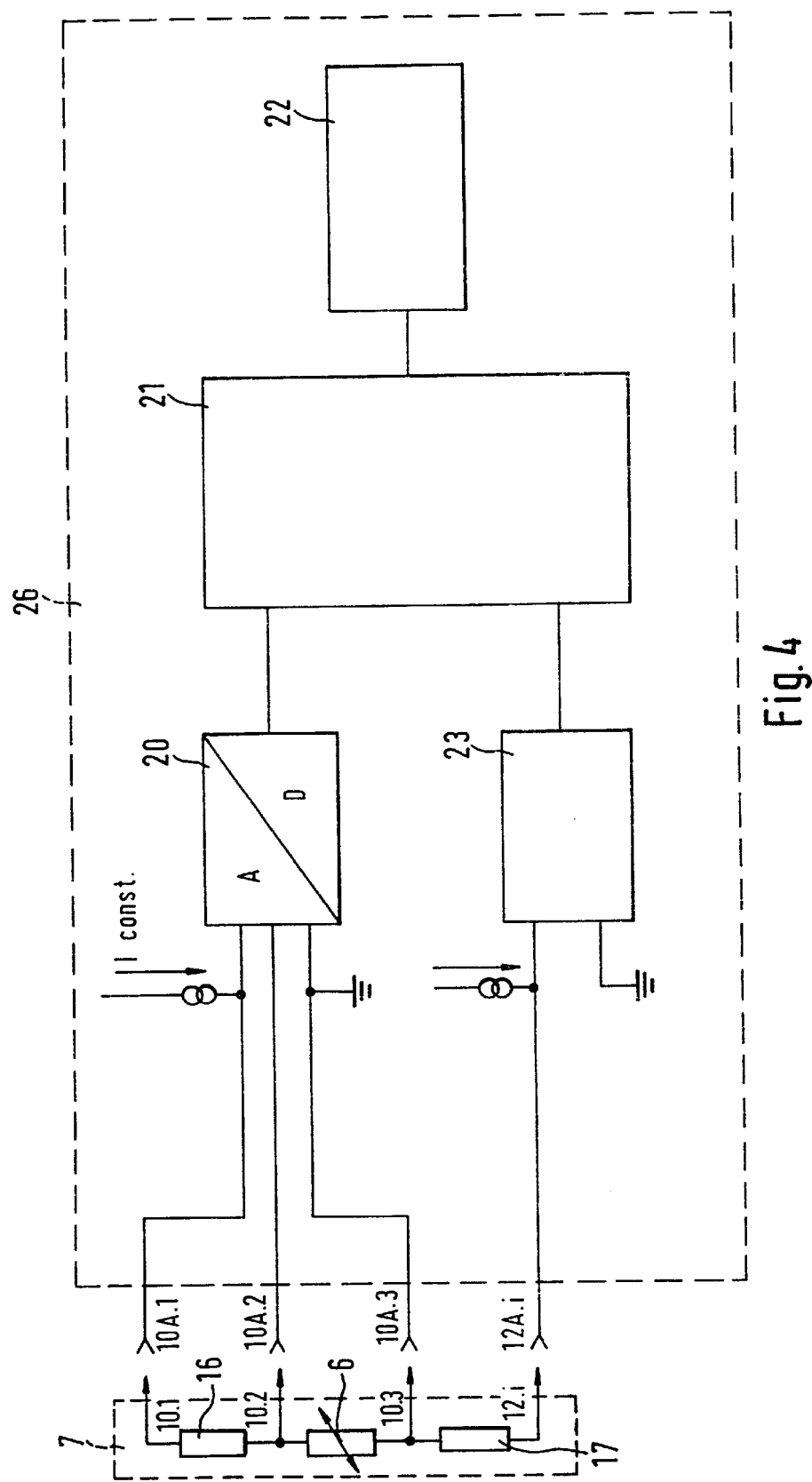
FIGS. 4, 5, and 6 show schematic embodiments of circuits employed in a connector assembly and connected processing unit according to the invention.
Figure 5:
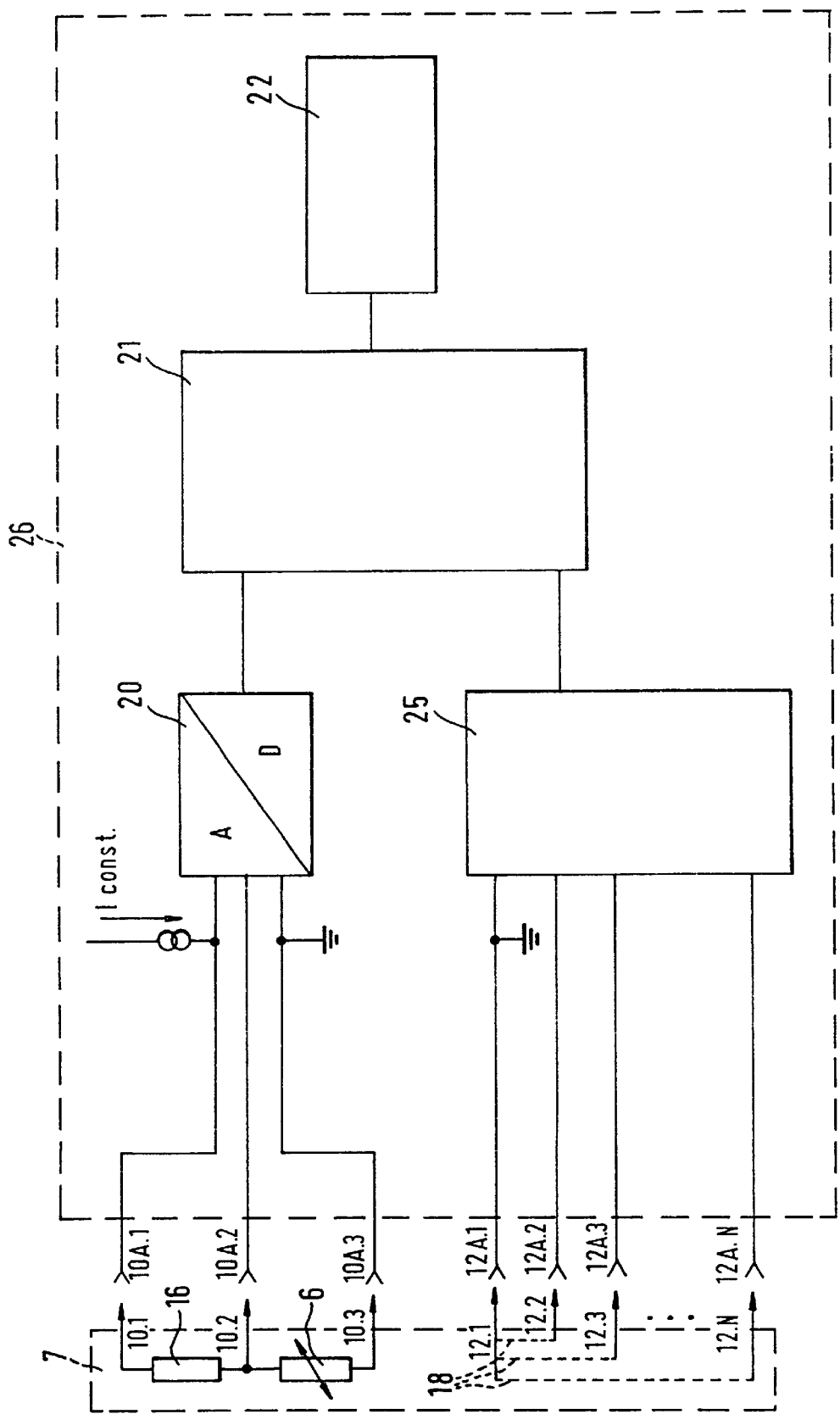
Figure 6:
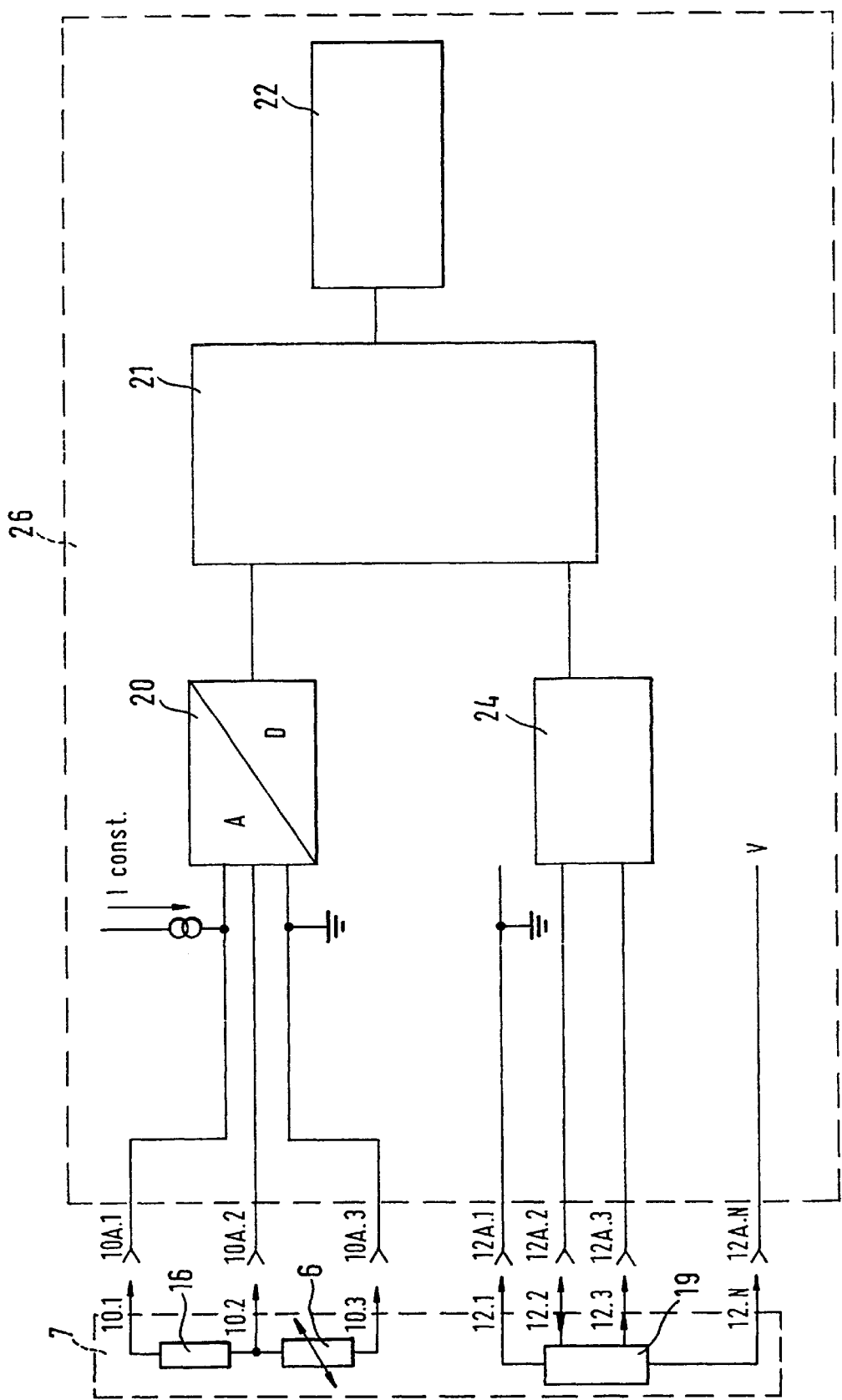

FIGS. 4, 5, and 6 show preferred schematic embodiments of catheter encoding and decoding circuits according to the invention, in connection to a signal processing unit 26.

Common to FIGS. 4, 5 and 6, the connector 7 comprises three electrical pins 10.1, 10.2, and 10.3 dedicated to provide electrical signals representing one or more physiological parameter(s), e.g. from a blood temperature sensing circuitry comprising the thermistor 6 (cf. FIGS. 1 and 2) and a linearization resistor 16.

A signal processing unit 26 provides corresponding pins 10A.1, 10A.2, and 10A.3 adapted to receive the contact or electrical pins 10.1, 10.2, and 10.3 of the connector 7. In a preferred embodiment, the signal processing unit 26 comprises an AD-converter 20 coupled to pins 10A.1, 10A.2, and 10A.3, an output thereof being coupled to a digital processing device 21 for computing and displaying the measurement results by an output display 22. In the example of the thermodilution catheter 2, the AD-converter 20 and the digital processing device 21 represent the blood temperature channel.

According to the invention, the site of an application of the catheter 2 and/or the effect of the respective application site of the catheter 2 on the measuring parameter(s) is coded.

For encoding purposes, one or more additional electrical pins 12.i (i=1, 2, 3, . . . , n) of the connector 7 of the catheter 2 are used for connecting respective encoding means 17, 18, or 19, which are preferably located in a housing of the connector 7 of the catheter 2.

For decoding purposes, the one or more additional electrical pins 12A.i (i=1, 2, 3, . . . , n) of the signal processing unit 26 correspond to and are adapted to receive the electrical pins 12.i (i=1, 2, 3, . . . , n) of the connector 7 of the catheter 2 and are coupled to respective decoding means 23, 24, or 25, which are preferably located in a housing of the signal processing unit 26. The respective decoding means 23, 24, or 25 are coupled to a digital processing device 21 for selecting the appropriate algorithms and display modes for computing and displaying the dedicated measurement results of the catheter 2 without intervention of a user. The embodiment of FIG. 4 provides analog encoding and decoding means. The encoding means 17 is embodied by an impedance bridge 17, such as a resistance, capacitive, and/or inductive bridge, between the pins 10.3 and 12.1 of the catheter connector 7. For the example of the thermodilution catheter 2, the encoding of the catheter site might be accomplished by an impedance bridge 17 e.g. according but not limited to the following matrix:

| Catheter placement site | Resistance between pins 10.3 and 12.1 |
|---|---|
| undetermined access | 0R |
| femoral artery access | 1R |
| axillary artery access | 2R |
| radial artery access | 3R |
| . | . |
| . | . |
| . | . |
| left subclavian vein access | 00R |

The voltage drop across the impedance bridge 17 is digitized by an AD-converter 23 and is used for decoding the dedicated cardiovascular access by software in the digital processing device 21.

In the embodiment of FIG. 5, a digital encoding and decoding is provided using conducting bridging members 18 as encoding means between pins 12.1, 12.2, 12.3 at minimum, which may be extended to n pins depending on the number of distinguishable sites of the catheter 2, e.g. 2* using binary code. For the example of the thermodilution catheter 2, the encoding of the catheter site might be accomplished e.g. according to the following matrix:

| | Pins | | |
|---|---|---|---|
| Catheter placement site | 12.1–12.2 | 12.1–12.3 | 12.1–12.4 |
| undetermined access | closed | closed | closed |
| femoral artery access | open | closed | closed |
| axillary artery access | closed | open | closed |
| radial artery access | open | open | closed |
| . | . | . | . |
| . | . | . | . |
| . | . | . | . |
| left subclavian vein access | open | open | open |

The presence or absence of the conductive bridge members 18 defines the catheter access site decoded by the digital decoding circuitry 25 and communicated to the digital processing device 21.

FIG. 6 shows the encoding and decoding means provided by a digital memory 19, preferably a read only memory ROM or a shift register with encoded inputs, connected to pins 12.1, 12.2, 12.3 or further pins 12.i, if required, of the connector 7 of the catheter 2. Such a solution is especially useful if encoding of more than 2* information are needed, with n greater than the available number of electrical pins 12.i. A digital memory of e.g. n bit size with serial output is capable to encode up to 2* different catheter access sites, which can be decoded by a decoding circuitry 24 communicating with the digital processing device 21. The decoding circuitry can also be realized as part of the digital processing device, e.g. by software. At minimum the digital memory 19 has to be read out at power on of the signal-processing unit 26 and with every connection of a medical device 2. By decoded information the appropriate algorithms and display modes is selected for computing and displaying the dedicated measurement results of the catheter 2.

| Catheter placement site | Binary coding with n = 4 | | | |
|---|---|---|---|---|
| left subclavian vein access | H | H | H | H |
| femoral artery access | H | H | H | L |
| axillary artery access | H | H | L | H |
| radial artery access | H | H | L | L |
| . | . | . | . | . |
| . | . | . | . | . |
| . | . | . | . | . |
| undetermined access | L | L | L | L |

The decoded information is used in the processing device 21 to select the right algorithms and display modes for computing and displaying the dedicated measurement results of the encoded catheter without intervention of a user.

What is claimed is:

1. A connector for connecting a catheter to a processing device for processing a physiological parameter measured by the catheter, said catheter capable of being introduced into a patient's body, said connector comprising:
   at least one of a device for coding the site of an application of said catheter in the patient's body and a device for coding the effect of the site of an application of said catheter in the patient's body on the measurement of the physiological parameter; and
   a plurality of contacts for providing a signal representing the physiological parameter and one or more additional contacts for connecting at least one of said devices for coding.

2. The connector of claim 1, wherein at least one of said devices for coding comprises an impedance bridge, wherein said impedance bridge comprises at least one of:
   a resistance bridge, a capacitive bridge, an inductive bridge, and conductive bridging members.

3. The connector of claim 1, wherein said connector is for introduction into a patient's blood vessel.

4. The connector of claim 2, wherein the encoding means comprises a memory.

5. The catheter of claim 7, wherein said catheter is form introduction into a patient's blood vessel.

6. The catheter of claim 7, further comprising a thermodilution catheter dedicated for specific physiological measurements and comprising temperature sensing means.

7. A catheter for introduction into a patient's body for measuring a physiological parameter, said catheter comprising:
   an elongate body for introduction into said patient's body;
   a sensor for measuring said physiological parameter; and
   a device for coding at least one of:
      the site of an application of the catheter in the patient's body and the effect of the site of an application of the catheter in the patient's body on the measurement of the physiological parameter.

8. The catheter of claim 7, wherein said device for coding further comprises a connector for connecting said catheter to a processing device that processes a physiological parameter measured by the catheter.

9. A processing device for processing a measured physiological parameter received from a catheter according to claim 7, wherein said processing device comprises at least one of:
   a device for coding or decoding the site of an application of the catheter in the patient's body and a device for coding or decoding the effect of the site of an application of the catheter in the patient's body on the measurement of the physiological parameter.

10. The processing device of claim 9, further comprising a plurality of electrical contacts, for receiving an electrical signal representing the physiological parameter from a catheter according to claim 4, and one or more additional electrical contacts for connecting at least one of said devices for coding or decoding to the catheter.

11. The processing device of claim 10, further comprising decoding circuitry connectable to one or more of the additional electrical contacts.

12. A method for measuring a physiological parameter, comprising the steps of:

(a) introducing a catheter into a patient's body, (b) measuring the physiological parameter, and (c) providing the measured physiological parameter together with at least one of:

the coded site of an application of the catheter in the patient's body and the coded effect of the site of an application of the catheter in the patient's body on the measurement of the physiological parameter.

13. The method of claim 11 further comprising a step of:

(d) processing the measured physiological parameter in accordance with at least one of:

the coded site of an application of the catheter in the patient's body and the coded effect of the site of an application of the catheter in the patient's body on the measurement of the physiological parameter.

14. The method of claim 12, wherein said step of introducing a catheter into a patient's body further comprises introducing a catheter into the patient's blood vessel.

15. A method comprising the steps of:

a) measuring a physiological parameter at a first spatial location of a measuring catheter within a patient's body, b) encoding the first spatial location of the measuring catheter, and c) automatically setting characteristic measurement parameters for a measurement evaluation algorithm dependent on the encoded first spatial location of the measuring catheter, so that the measurement evaluation algorithm takes the first spatial location of the measuring catheter into consideration.

16. The method of claim 15, wherein the step (a) of measuring the physiological parameter comprises a step of sensing at the first spatial location a temperature displacement caused by an injection of a cold bolus of a thermal dilution catheter at a second spatial location upstream from the first spatial location.

17. The method of claim 15, further comprising at least one of:

a step of optimizing and a step of adapting the measuring behavior of the catheter in accordance with the encoded first spatial location.

18. The method according to claim 15, further comprising a step of correcting signal modifications due to influences of the encoded first spatial location.

19. The method according to claim 15, further comprising a step of enabling or disabling specific measuring or measurement evaluation modules for providing specific results dependent on the encoded first spatial location.

20. The method according to claim 15, further comprising a step of adapting the measurement on the specific conditions and influences of the encoded first spatial location.

21. The method of 20, further comprising a step of evaluating the measurement results evaluated in accordance with the setting of the encoded first spatial location by adapting a sensing resolution to a signal strength at the encoded first spatial location.

22. The method of claim 16, wherein the first spatial location of the temperature sensing represents the access site of the thermodilution catheter.

* * * * *